United States Patent
Kim et al.

(10) Patent No.: US 11,363,989 B2
(45) Date of Patent: Jun. 21, 2022

(54) ELECTRONIC DEVICE, SIGNAL PROCESSING METHOD THEREOF, BIOLOGICAL SIGNAL MEASUREMENT SYSTEM, AND NON-TRANSITORY COMPUTER READABLE RECORDING MEDIUM

(71) Applicant: SAMSUNG ELECTRONICS CO., LTD., Suwon-si (KR)

(72) Inventors: Hyung-soon Kim, Goyang-si (KR); Kwang-hyun Won, Bucheon-si (KR); Min-hyoung Lee, Seongnam-si (KR); Do-yoon Kim, Seongnam-si (KR); Chan-yul Kim, Seongnam-si (KR); Jea-hyuck Lee, Anyang-si (KR); Jae-geol Cho, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 676 days.

(21) Appl. No.: 16/060,795

(22) PCT Filed: Oct. 6, 2016

(86) PCT No.: PCT/KR2016/011151
§ 371 (c)(1),
(2) Date: Jun. 8, 2018

(87) PCT Pub. No.: WO2017/099340
PCT Pub. Date: Jun. 15, 2017

(65) Prior Publication Data
US 2018/0360388 A1 Dec. 20, 2018

(30) Foreign Application Priority Data
Dec. 8, 2015 (KR) .......................... 10-2015-0174160

(51) Int. Cl.
*A61B 5/00* (2006.01)
*A61B 5/11* (2006.01)
(Continued)

(52) U.S. Cl.
CPC .......... *A61B 5/7232* (2013.01); *A61B 5/0002* (2013.01); *A61B 5/1118* (2013.01);
(Continued)

(58) Field of Classification Search
CPC ... A61B 5/7232; A61B 5/0002; A61B 5/0004; A61B 5/0006; A61B 5/726;
(Continued)

(56) References Cited

U.S. PATENT DOCUMENTS 5,442,351 A * 8/1995 Horspool ................ G06T 9/005
341/51
5,604,498 A * 2/1997 Park ........................ G06T 9/005
341/65
(Continued)

FOREIGN PATENT DOCUMENTS

JP 6-237908 A 8/1994
JP 2008-253378 A 10/2008
(Continued)

OTHER PUBLICATIONS

M. Sabarimalai Manikandan, S. Dandapat, Wavelet-based electrocardiogram signal compression methods and their performances: A prospective review, 2014, Biomedical Signal Processing and Control 14, 73-107 (Year: 2014).*
(Continued)

*Primary Examiner* — Alexander Satanovsky
(74) *Attorney, Agent, or Firm* — Sughrue Mion, PLLC

(57) ABSTRACT

Provided are an electronic device, a signal processing method thereof, a biological signal measurement system, and a non-transitory computer readable recording medium.
(Continued)

The electronic device, according to one embodiment of the present disclosure, comprises: a sensor for measuring a biological signal of a user; and a processor for determining the periodicity of the measured biological signal, and selectively compressing the measured biological signal according to the determined periodicity.

12 Claims, 15 Drawing Sheets

(51) Int. Cl.
| | |
|---|---|
| *A61B 5/024* | (2006.01) |
| *A61B 5/1455* | (2006.01) |
| *A61B 5/318* | (2021.01) |
| *A61B 5/332* | (2021.01) |
| *A61B 5/352* | (2021.01) |
| *A61B 5/369* | (2021.01) |
| *A61B 5/389* | (2021.01) |
| *A61B 5/398* | (2021.01) |
| *A61B 5/0205* | (2006.01) |

(52) U.S. Cl.
CPC .......... *A61B 5/1123* (2013.01); *A61B 5/6801* (2013.01); *A61B 5/024* (2013.01); *A61B 5/0205* (2013.01); *A61B 5/02416* (2013.01); *A61B 5/1455* (2013.01); *A61B 5/318* (2021.01); *A61B 5/332* (2021.01); *A61B 5/352* (2021.01); *A61B 5/369* (2021.01); *A61B 5/389* (2021.01); *A61B 5/398* (2021.01); *A61B 5/4809* (2013.01); *A61B 5/681* (2013.01); *A61B 5/7285* (2013.01); *A61B 2562/0219* (2013.01)

(58) Field of Classification Search
CPC . A61B 5/04012; A61B 5/0452; A61B 5/7207; A61B 5/1123; A61B 5/6801; A61B 5/1118; A61B 5/4809; A61B 5/0456; A61B 5/02416; A61B 5/0496; A61B 2562/0219; A61B 5/0205; A61B 5/0476; A61B 5/0488; A61B 5/681; A61B 5/0402; A61B 5/024; A61B 5/0404; A61B 5/7285; G06F 21/32
See application file for complete search history.

(56) References Cited

U.S. PATENT DOCUMENTS

| | | | |
|---|---|---|---|
| 8,632,465 B1* | 1/2014 | Brockway | G06K 9/0053 600/300 |
| 9,364,160 B2 | 6/2016 | Marziliano et al. | |
| 2002/0065473 A1* | 5/2002 | Wang | A61B 5/02405 600/518 |
| 2011/0015467 A1* | 1/2011 | Dothie | A61B 5/4815 600/26 |
| 2012/0259182 A1 | 10/2012 | Kim et al. | |
| 2013/0261482 A1 | 10/2013 | Marziliano et al. | |
| 2014/0005988 A1 | 1/2014 | Brockway | |
| 2015/0005655 A1* | 1/2015 | Sato | A61B 5/0006 600/521 |
| 2015/0169462 A1* | 6/2015 | Vaisanen | G06F 12/0246 711/166 |
| 2015/0289823 A1* | 10/2015 | Rack-Gomer | A61B 5/165 600/365 |
| 2016/0015289 A1* | 1/2016 | Simon | A61B 5/04842 600/301 |
| 2018/0064388 A1* | 3/2018 | Heneghan | A61B 5/11 |

FOREIGN PATENT DOCUMENTS

| | | |
|---|---|---|
| JP | 2010-269082 A | 12/2010 |
| JP | 2012-165979 A | 9/2012 |
| KR | 10-2009-0089039 A | 8/2009 |
| KR | 10-2010-0076648 A | 7/2010 |
| KR | 10-2012-0092797 A | 8/2012 |
| KR | 10-2012-0113530 A | 10/2012 |
| KR | 10-2014-0139564 A | 12/2014 |
| KR | 10-2015-0103568 A | 9/2015 |
| WO | 2014/138414 A1 | 9/2014 |

OTHER PUBLICATIONS

Patrick S. Hamilton and Willis J. Tompkins, Compression of the Ambulatory ECG by Average Beat Subtraction and Residual Differencing, Mar. 1991, IEEE Transactions on Biomedical Engineering. vol. 38. No. 3. p. 253-259. (Year: 1991).*
International Search Report dated Jan. 6, 2017, issued by the International Searching Authority in counterpart International Patent Application No. PCT/KR2016/011151 (PCT/ISA/210).
Written Opinion dated Jan. 6, 2017, issued by the International Searching Authority in counterpart International Patent Application No. PCT/KR2016/011151 (PCT/ISA/237).
Communication dated Jun. 21, 2021, issued by the Korean Intellectual Property Office in Korean Patent Application No. 10-2015-0174160.
Communication dated Dec. 11, 2021 by the Korean Intellectual Property Office in Korean Patent Application No. 10-2015-0174160.

* cited by examiner

ELECTRONIC DEVICE, SIGNAL PROCESSING METHOD THEREOF, BIOLOGICAL SIGNAL MEASUREMENT SYSTEM, AND NON-TRANSITORY COMPUTER READABLE RECORDING MEDIUM

TECHNICAL FIELD

Apparatuses and methods consistent with the present disclosure relates to an electronic device, a signal processing method thereof, a biological signal measurement system, and a non-transitory computer readable recording medium, and more particularly to an electronic device whose efficiency is improved by compressing a measured biological signal, a signal processing method thereof, a biological signal measurement system, and a non-transitory computer readable recording medium.

BACKGROUND ART

Technology for measuring biological signals in accordance with the development of electronic technology has been also developing. In particular, technology for continuously measuring a biological signal of a user through an electronic device worn by the user on a daily basis, such as a wearable device, has been developed.

However, as a biological signal measurement device routinely measures the biological signal of the user, an amount of biological signal data is explosively increasing. Also, problems of data security also arise when biological signals are stored or transmitted to external devices.

Accordingly, a method of compressing a biological signal has been studied. However, the conventional biological signal compression method has a limitation that it merely suggests a compression algorithm. Therefore, pre-conditions for the implementation of the compression algorithm may not be determined, which rather caused a problem of an increase in the capacity of data due to the application of the compression algorithm.

DISCLOSURE

Technical Problem

The present disclosure provides an electronic device that selectively compresses a biological signal by determining whether to compress the biological signal according to the biological signal and a motion of a user, a signal processing method thereof, a biological signal measurement system, and a non-transitory computer readable recording medium.

Technical Solution

According to an aspect of the present disclosure, an electronic device includes: a sensor configured to measure a biological signal of a user; and a processor configured to determine a periodicity of the measured biological signal and selectively compress the measured biological signal according to the determined periodicity.

The electronic device may further include a motion sensor configured to sense a degree of motion of the user, wherein when the detected degree of motion is less than or equal to a predetermined threshold value and the measured biological signal has the periodicity, the processor is configured to compresses the measured biological signal.

The processor may be configured to detect a plurality of peaks from the measured biological signal and determine the periodicity of the biological signal based on intervals between the detected plurality of peaks.

The processor may be configured to generate a differential signal by using an average value of the measured biological signals and compress the biological signals by using the generated differential signal and a number of bits for representing the generated differential signal.

When a predetermined number of biological signals are measured, the processor may be configured to determine a periodicity of the measured predetermined number of biological signals.

The processor may be configured to monitor compression efficiency using the compressed biological signal and stop compressing the measured biological signal when the compression efficiency is less than or equal to a predetermined level.

The electronic device may further include a communicator configured to communicate with an external device, wherein the processor is configured to control the communicator to transmit the compressed biological signal.

The electronic device may further include a storage configured to store the compressed biological signal.

The biological signal may be at least one of an ECG, an EEG, an EMG, an EOG, and a PPG.

The sensor may be configured to measure a plurality of kinds of biological signals of the user, and wherein the processor is configured to compress the measured plurality of kinds of biological signals together.

According to another aspect of the present disclosure, an electronic device includes a sensor configured to measure a biological signal of a user; a motion sensor configured to sense a degree of motion of the user; and a processor configured to compress the measured biological signal when the sensed degree of motion is less than or equal to a predetermined threshold value.

The motion sensor may include an acceleration sensor and is configured to determine a state of the user as one of a sleep state, a rest state, a walking state, and a running state based on a value measured by the acceleration sensor.

According to another aspect of the present disclosure, a biological signal measurement system includes a biological signal measurement device configured to measure a biological signal of a user and a state of motion of the user and an analysis device configured to analyze the biological signal, wherein the biological signal measurement device is configured to selectively compress the measured biological signal based on the measured biological signal and state of motion and transmit the compressed biological signal to the analysis device, and the analysis device is configured to decompress the transmitted biological signal to analyze the measured biological signal.

According to another aspect of the present disclosure, a signal processing method of an electronic device includes measuring a biological signal of a user; determining a periodicity of the measured biological signal; and selectively compressing the measured biological signal according to the determined periodicity.

The signal processing method may further include: sensing a degree of motion of the user, wherein the compressing includes: when the sensed degree of motion is less than or equal to a predetermined threshold value and the measured biological signal has the periodicity, compressing the measured biological signal.

The determining of the periodicity may include: detecting a plurality of peaks from the measured biological signal; and determining the periodicity of the biological signal based on intervals between the detected plurality of peaks.

The selectively compressing may include generating a differential signal using the average value of the measured biological signal and compressing the biological signal using the generated differential signal and the number of bits for representing the generated differential signal.

According to another aspect of the present disclosure, a signal processing method of an electronic device includes measuring a biological signal of a user; sensing a degree of motion of the user; and compressing the measured biological signal when the sensed degree of motion is less than or equal to a predetermined threshold value.

The sensing of the degree of motion of the user may include measuring the degree of motion of the user using an acceleration sensor and determining a state of the user as one of a sleep state, a rest state, a walking state, and a running state based on a value measured by the acceleration sensor.

According to another aspect of the present disclosure, a non-transitory computer readable recording medium including a program for executing a signal processing method of an electronic device includes measuring a biological signal of a user; determining a periodicity of the measured biological signal; and selectively compressing the measured biological signal according to the determined periodicity.

Advantageous Effects

According to the diverse exemplary embodiments of the present disclosure, the compression efficiency of biological signal data may be improved.

BEST MODE

Hereinafter, exemplary embodiments of the present disclosure will be described in detail with reference to the accompanying drawings. In the following description of the present disclosure, detailed description of known functions and configurations incorporated herein will be omitted when it may obscure the subject matter of the present disclosure. The following terms are defined in consideration of the functions of the present disclosure and may vary depending on a user, an operator, or a custom. Therefore, the definition should be based on the contents throughout the present specification.

Terms including ordinals such as first, second, etc. may be used to describe various elements, but the elements are not limited by the terms. Terms are used only for the purpose of distinguishing one element from another. For example, without departing from the scope of the present disclosure, a first element may be referred to as a second element, and similarly, the second element may also be referred to as the first element. The term "and/or" includes any combination of a plurality of related items or any of a plurality of related items.

The terms used herein are used to describe the embodiments and are not intended to restrict and/or to limit the disclosure. The singular forms "a," "an," and "the" include plural expressions unless the context clearly dictates otherwise. In the present specification, terms such as "comprise," "include," and the like are intended to specify the presence of stated features, numbers, operations, elements, components, or combinations thereof, but do not preclude the presence or addition of one or more other features, numbers, operations, elements, components, or combinations thereof.

Figure 1:
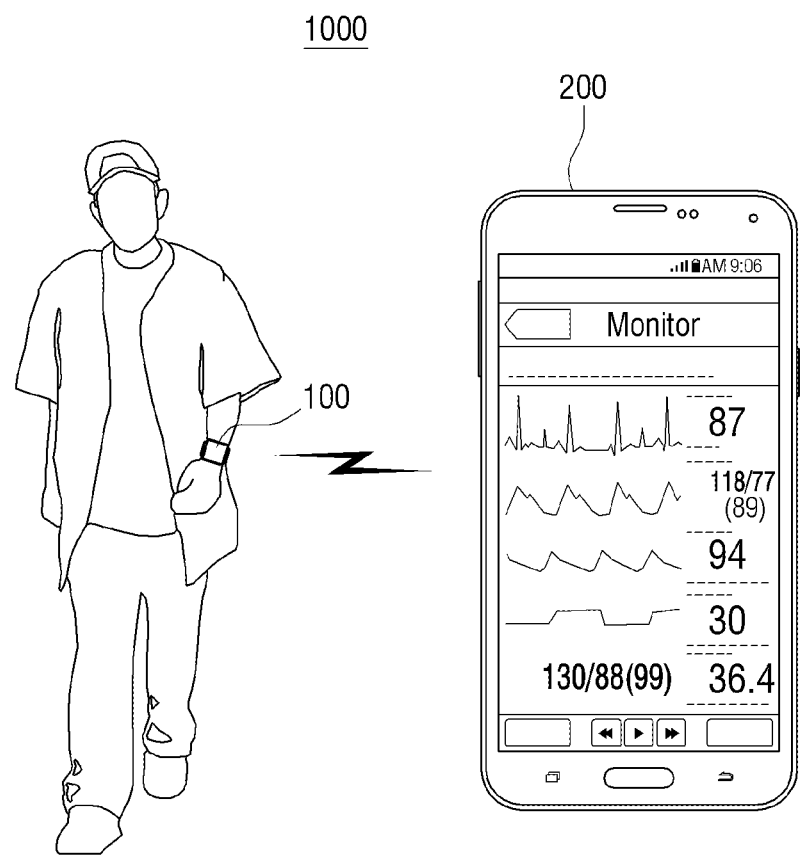
FIG. 1 is a conceptual diagram showing a biological signal measurement system according to an exemplary embodiment of the present disclosure.

FIG. 1 is a diagram showing a biological signal measurement system 1000 according to an exemplary embodiment of the present disclosure. Referring to FIG. 1, the biological signal measurement system 1000 may include a biological signal measurement device 100 and an analysis device 200. In the present specification, it is noted that the biological signal measurement device 100 may be described as the electronic device 100, and the analysis device 200 may be described as the external device 200.

The biological signal measurement device 100 according to an exemplary embodiment of the present disclosure may continuously measure a biological signal of a user. In the embodiment of FIG. 1, the biological signal measurement device 100 is implemented in the form of a smart watch, which is a kind of wearable device, but is not limited thereto. For example, the biological signal measurement device 100 may be implemented in various forms such as a patch, a pair of glasses, a hat, a headband, earphones, and a headset. Examples of biological signals that may be measured by the biological signal measurement device 100 may include electrocardiogram (ECG), electroencephalography (EEG), electromyography (EMG), electrooculography (EOG), and photoplethsmography (PPG). However, the biological signals that may be measured by the biological signal measurement device 100 are not limited to the above examples.

The analysis device 200 according to an exemplary embodiment of the present disclosure may analyze the biological signal measured by the biological signal measurement device 100. In the embodiment of FIG. 1, the analysis device 200 is implemented as a smartphone, but is not limited thereto. For example, the analysis device 200 may be implemented in various forms such as a tablet, a PC, a laptop, and the like.

According to an exemplary embodiment of the present disclosure, the biological signal measurement device 100 may measure the biological signal and a motion of the user. The biological signal measurement device 100 may determine whether to compress the measured biological signal based on at least one of the measured biological signal and a motion state. For example, when the measured biological signal is periodic or when the motion of the user is small, the biological signal measurement device 100 may compress the measured biological signal. When the measured biological signal is an aperiodic signal or when the motion of the user is great, in the case where the biological signal measurement device 100 performs data compression, the compression efficiency is lowered. Even with a specific compression algorithm, a problem has been found that an amount of data increases due to the compression. A specific reference for determination of the compression performance of the biological signal measurement device 100 will be described later. Then, the biological signal measurement device 100 may store the compressed or uncompressed biological signal data or may transmit the data to the analysis device 200.

The analysis device 200 may receive the compressed or uncompressed biological signal data from the biological signal measurement device 100. For example, the analysis device 200 may receive and decompress the compressed biological signal data from the biological signal measurement device 100. Then, the analysis device 200 may post-process or analyze the decompressed biological signal data.

According to the biological signal measurement system 1000 according to an exemplary embodiment of the present disclosure as described above, the storage of the data or an amount of transmitted data may be reduced by increasing the compression efficiency. Accordingly, this results in reduction of power consumption, reduction of data transfer time, and reduction of required memory capacity, etc.

Figure 2:
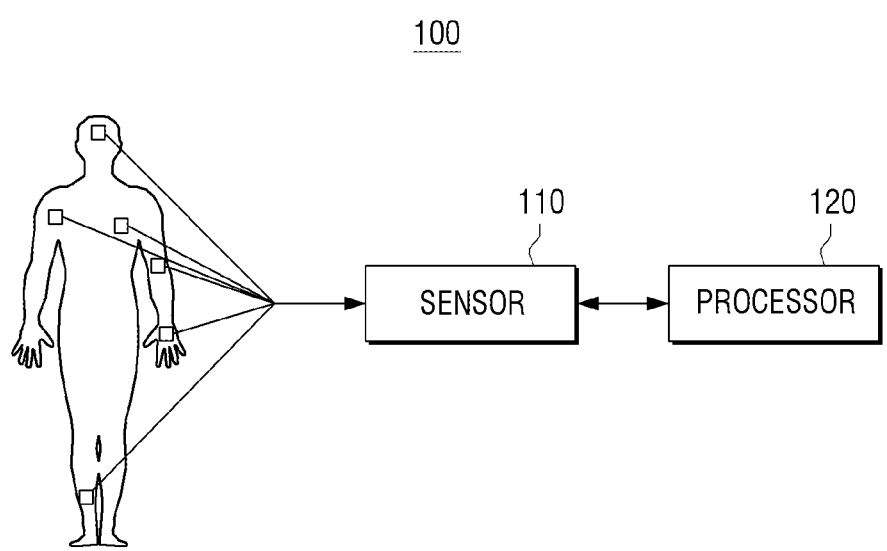
FIG. 2 is a block diagram schematically explaining a configuration of an electronic device according to an exemplary embodiment of the present disclosure.

FIG. 2 is a block diagram schematically explaining a configuration of the electronic device 100 according to an exemplary embodiment of the present disclosure. Referring to FIG. 2, the electronic device 100 may include a sensor 110 and a processor 120.

The sensor 110 may measure a biological signal of a user. The sensor 110 may be implemented in various types of analog front end (AFE). The electronic device 100 may be implemented to be worn on various body parts of the user, and thus the sensor 110 may measure various biological signals in contact with the body of the user wearing the electronic device 100.

The processor 120 may determine the periodicity of the measured biological signal. The processor 120 may selectively compress the measured biological signal according to the determined periodicity. For example, when the measured biological signal has a periodic peak, the processor 120 may compress the measured biological signal. This is because compressing a periodic signal is much higher in the data compression efficiency than compressing an aperiodic signal.

In the case of a signal from which a peak may be periodically detected among biological signals, the processor 120 may detect a plurality of peaks from the measured biological signal to determine whether the measured biological signal is a periodic signal. When there is only a fluctuation within a predetermined range of intervals between the plurality of peaks, the processor 120 may determine that the measured biological signal is the periodic signal. To the contrary, when the peak is aperiodically detected or the peak cannot be detected, the processor 120 may determine that the measured biological signal is the aperiodic signal.

When it is determined that the measured biological signal is the periodic signal, the processor 120 may compress the biological signal. The processor 120 may store the compressed biological signal or transmit the compressed biological signal to the external device 200. For example, the processor 120 may generate a differential signal using an average value of the measured biological signal. The processor 120 may compress the biological signal using the generated differential signal and the number of bits for expressing the generated differential signal.

As described above, the electronic device 100 according to an exemplary embodiment of the present disclosure may apply pre-conditions for the measured biological signal data compression. Accordingly, the electronic device 100 may perform data compression only when the data compression is more efficient, which produces an effect of an increase in the compression efficiency.

Figure 3:
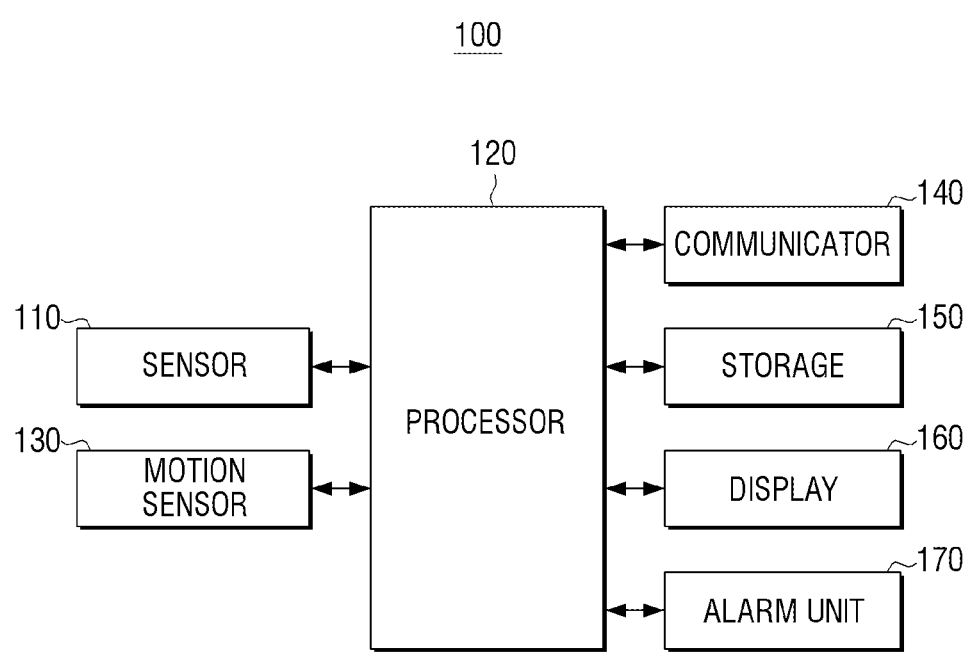
FIG. 3 is a diagram for in detail explaining a configuration of an electronic device according to an exemplary embodiment of the present disclosure.

FIG. 3 is a diagram for in detail explaining a configuration of the electronic device 100 according to an exemplary embodiment of the present disclosure. Referring to FIG. 3, the electronic device 100 may include the sensor 110, the processor 120, a motion sensor 130, a communicator 140, a storage 150, a display 160, and an alarm unit 170.

The sensor 110 may be implemented with various types of AFE to measure a plurality of kinds of biological signals. The sensor 110 may measure various biological signals by contacting a user's body wearing the electronic device 100. For example, the sensor 110 may measure at least one of an ECG, an EEG, an EMG, an EOG, and a PPG.

The motion sensor 130 may sense a degree of motion of the user. For example, when the detected degree of motion of the user is less than or equal to a predetermined threshold value, the processor 120 may compress the biological signal measured by the sensor 110. To the contrary, when the detected degree of motion of the user is equal to or greater than the predetermined threshold value, the processor 120 may not compress the biological signal measured by the sensor 110 but transmit the measured biological signal to the external device 200 or store the measured biological signal in the storage 150.

The motion sensor 130 may determine a motion state of the user. For example, the motion sensor 130 may include an acceleration sensor. Due to the characteristic of the biological signal, when the motion of the user is increased, the periodicity of the biological signal is degraded. That is, even if the biological signal is determined to be a periodic biological signal when the user remains in a place, the periodicity of the biological signal is significantly reduced when the motion of the user is increased.

The acceleration sensor senses a variation in speed with respect to a unit time. The acceleration sensor may be implemented in three axes. When the acceleration sensor is implemented as a three-axis acceleration sensor, the acceleration sensor is provided with X, Y, and Z-axis acceleration sensors arranged in different directions and orthogonal to each other.

The acceleration sensor converts an output value of each of the X, Y, and Z axis acceleration sensors into a digital value and provides the digital value to a preprocessor. At this time, the preprocessor may include a chopping circuit, an amplification circuit, a filter, and an A/D converter. Accordingly, an electric signal output from the three-axis acceleration sensor is chopped, amplified, and filtered, and then converted into a digital voltage value.

The motion sensor 130 may further include an angular velocity sensor, a geomagnetic sensor, and the like in addition to the acceleration sensor. By combining values measured by a plurality of types of sensors, the motion sensor 130 may more accurately determine the motion state of the user.

The angular velocity sensor detects an angular velocity by sensing a variation in a predetermined direction of the electronic device 100 during the unit time. A gyroscope having three axes may be used as the angular velocity sensor.

The geomagnetic sensor is a sensor capable of sensing an azimuth angle by sensing the flow of a magnetic field. The geomagnetic sensor may detect azimuth coordinates of the electronic device 100 and may detect a direction in which the electronic device 100 is placed based on the azimuth coordinates.

The geomagnetic sensor senses geomagnetism by measuring a voltage value induced by geomagnetism using a flux-gate or the like. The geomagnetic sensor may be implemented in two or three axes. In this case, since a geomagnetism output value calculated by each axis geomagnetic sensor varies according to the magnitude of a surrounding magnetic field, it is general to perform normalization to map the geomagnetism output value within a predetermined range (for example, −1 to 1). Normalization is performed using a normalization factor such as a scale value or an offset value. In order to calculate the normalization factor, an output value should be calculated by rotating the geomagnetic sensor several times and then detecting the maximum value and the minimum value of the output value. The normalized value using the normalization factor is used for an azimuth correction operation.

The communicator 140 may communicate with the external device 200 by wired or wirelessly. For example, the communicator 140 may transmit compressed biological signal data to the external device 200.

For example, the communicator 140 may use various wireless communication methods such as NFC (Near Field Communication), wireless LAN (Wireless LAN), IR (Infra-Red) communication, Zigbee communication, WiFi, Bluetooth, etc. The communicator 140 may use various wired communication methods such as a high definition multimedia interface (HDMI), a low voltage differential signaling (LVDS), a local area network (LAN), a universal serial bus (USB), etc.

Also, the communicator 140 may transmit and receive data to and from a hospital server connected through the medical image information system (PACS) or other medical devices in a hospital. Also, the communicator 140 may perform data communication according to the DICOM (Digital Imaging and Communications in Medicine) standard.

The storage 150 may store the measured biological signal or the compressed biological signal. Also, the storage 150 may store various data, programs, or applications that drive and control the electronic device 100. The storage 150 is a storage medium storing various programs and the like necessary for operating the electronic device 100 and may be implemented as a flash memory, a hard disk, or the like. For example, the storage 150 may be implemented in the form of an SD card.

The storage 150 may include a ROM for storing a program for performing an operation of the electronic device 100, a RAM for temporarily storing data according to the operation of the electronic device 100, and the like. Also, the storage 150 may further include an EEPROM (Electrically Erasable and Programmable ROM) for storing various reference data.

The display 160 may display a screen about the measured biological signal. For example, the display 160 may display measured electrocardiogram information on the screen in the form of a graph with respect to time. Also, the display 160 may display a UI providing additional information about the measured biological signal.

Also, the display 160 may display a screen capable of monitoring compression efficiency using the compressed biological signal. Also, the display 160 may display, in the form of a GUI, a button capable of controlling to stop compression of the measured biological signal when the compression efficiency is less than or equal to a predetermined level.

The display 160 may be implemented as a touch screen having a mutual layer structure together with a touch pad. The touch screen may receive user instructions through a touch input location, an area, a pressure of a touch input, and the like.

The alarm unit 170 may provide an alarm to the user. For example, the alarm unit 170 may provide a message to the user using a time signal, an auditory signal, a tactile signal, or the like. The message provided by the alarm unit 170 may include a message related to the operation of the electronic device 100, a message related to the measurement progress of the biological signal, a message regarding a result of analyzing the biological signal, and the like.

In addition, the electronic device 100 may further include a user input unit (not shown), a wireless charger (not shown), and the like.

The user input unit may receive input for controlling the electronic device 100 from the user. For example, the user input unit may be implemented as a key pad, a mouse, a touch panel, a touch screen, a track ball, a jog switch, or the like. The user input unit may be implemented as a voice recognition sensor, a fingerprint recognition sensor, a motion recognition sensor, or the like.

The wireless charger may charge power of the electronic device 100 using a magnetic induction method or a magnetic resonance method. The magnetic induction method is a technique of supplying a current by flowing the current through electromagnetic induction and inducing a magnetic field generated in a primary coil of a charging pad to a secondary coil provided in a charging target object. The magnetic resonance method is a technique of mounting a resonance coil of the same frequency on a charging pad and a charging target object, and applying power to a frequency using resonance. In particular, when the electronic device 100 is implemented as a portable device, the electronic device 100 may include the wireless charger. However, even if the electronic device 100 is implemented as the portable device, it may be implemented in various ways such as wired charging, power supply using a battery, and thus a power charging method of the electronic device 100 is not limited to a wireless charging method.

The processor 120 may control the overall configuration of the electronic device 100. The processor 120 may determine whether to compress the biological signal based on information measured in at least one of the sensor 110 and the motion sensor 130.

For example, the processor 120 may detect a plurality of peaks from the biological signal measured by the sensor 110, and determine whether the plurality of peaks occur at regular intervals. When it is determined that the plurality of peaks have a periodicity occurred at regular intervals, the processor 120 may compress the measured biological signal.

As another example, the processor 120 may determine the motion state of the user using the information measured by the motion sensor 130. When it is determined that the motion of the user is low, the processor 120 may compress the biological signal measured by the sensor 110.

As described above, the processor 120 may determine whether to perform compression based on at least one of the quality of biological information and the motion of the user, rather than compressing all of measured biological information. This selective compression directly affects the compression efficiency.

Figure 4A:
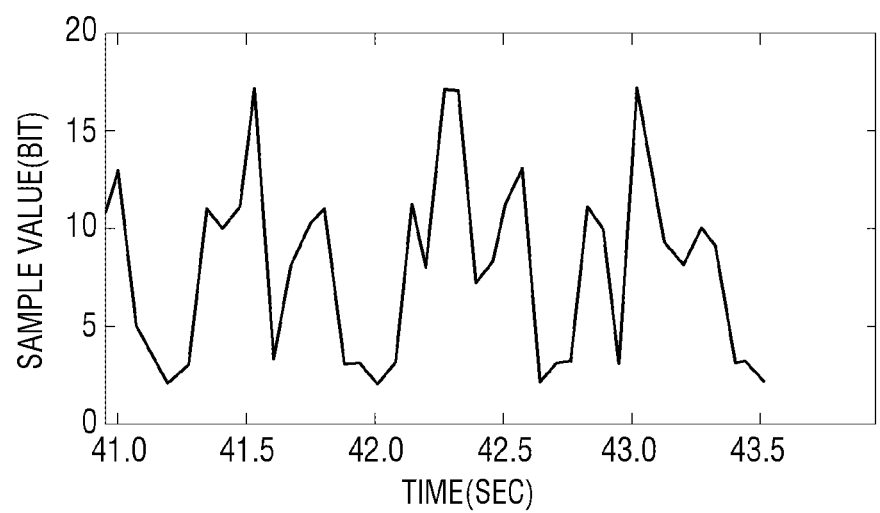
FIGS. 4A to 4C are graphs for explaining the size of data according to the compression of a biological signal.
Figure 4B:
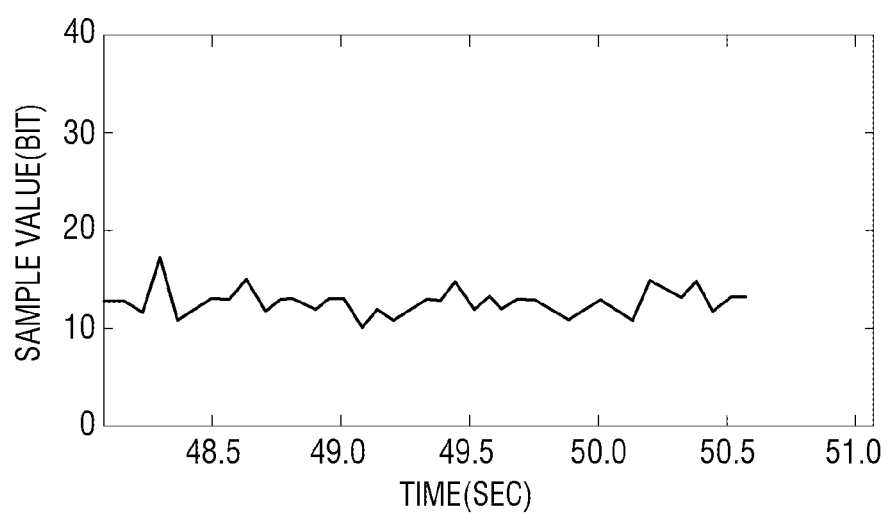
Figure 4C:
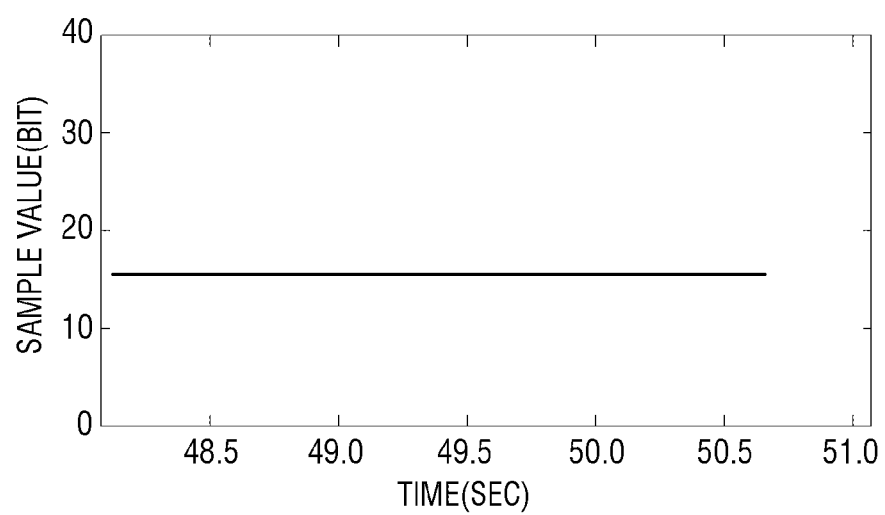

FIGS. 4A to 4C are diagrams for explaining the size of data according to the compression of a biological signal. FIG. 4A is a diagram of a result of compressing data when it is determined that the processor 120 compresses the data. FIG. 4B is a diagram of a result of forcibly compressing the data when it is determined that the processor 120 does not compress the data. FIG. 4C is a diagram of uncompressed data. Referring to FIG. 4C, it may be seen that the size of the uncompressed data is 16 bits.

For example, the processor 120 may compress a biological signal when the measured biological signal is determined to be periodic. Referring to FIG. 4A, the processor 120 may compress 16-bit data to produce data having a size of 5 to 16 bits.

FIG. 4B shows the result of forcibly compressing data when the measured biological signal is not periodic or when a motion of a user is large. Referring to FIG. 4B, it may be confirmed that the size of the compressed data is 12 to 19 bits. That is, it may be seen that the compression efficiency is remarkably low or the data size is rather increased.

That is, it may be seen that the effect of compression is significantly reduced when the electronic device 100 according to an exemplary embodiment of the present disclosure does not selectively compress the biological signal. Determining whether the processor 120 compresses data and a compression method will be described in more detail below.

Each of the above-described elements of the electronic device 100 according to various embodiments of the present disclosure may be composed of one or more components. Names of the elements may vary depending on a type of a device. The electronic device 100 according to various embodiments of the present disclosure may be configured to include at least one of the elements described above, with some elements omitted or further including additional elements. Also, some of the elements of the electronic device 100 according to various embodiments of the present disclosure may be combined and configured as an entity, thereby performing the same functions of the elements before being combined.

According to an exemplary embodiment of the present disclosure, in the case of a signal from which a peak may be periodically detected among biological signals, the processor 120 may determine whether to compress biological signal data according to whether to detect a periodic peak. Examples of the signal from which the peak may be periodically detected among biological signals include ECG and PPG.

Figure 5:
FIG. 5 is an ECG graph showing an example of a periodic biological signal.

FIG. 5 is a diagram showing an ECG signal which is an example of a periodic biological signal. ECG is a record of a cardiac electrical activity. Since a myocardium depolarizes every heartbeat, the sensor 110 may detect and amplify a fine electrical signal on the skin. Since a peak may be detected every heartbeat cycle, ECG corresponds to a typical periodic biological signal.

As shown in FIG. 5, the ECG signal is formed with three wavelengths of a P wave, a QRS wave, and a T wave. The P wave occurs when atrial depolarization occurs. The QRS wave occurs when depolarization of ventricle occurs. The T wave occurs when ventricle repolarizes. Since the largest peak in the ECG signal corresponds to an R peak, a cardiac cycle may be determined by an interval between R peaks. The interval between the R peaks is referred to as an RRI (R-R Interval).

According to an exemplary embodiment of the present disclosure, the processor 120 may detect the R peaks from a measured ECG signal. Then, the processor 120 may determine whether the measured ECG signal is a periodic biological signal based on an RRI value between the detected R peaks.

When the R peak may not be detected from the measured ECG signal, or when the R peaks occur aperiodically, the processor 120 may not compress the measured ECG signal. To the contrary, when the measured ECG signal is periodically generated as shown in FIG. 6, the processor 120 may compress the measured ECG signal.

Figure 6:
FIG. 6 is a diagram for explaining a method of determining a periodicity of a biological signal at intervals between a plurality of peaks.

Referring to FIG. 6, the processor 120 may detect six peaks from the measured biological signal. The processor 120 may then measure intervals t1, t2, t3, t4, and t5 between the peaks. For example, the processor 120 may determine that a periodic signal has been measured when the intervals between the peaks is within a 15% range. As shown in Equation 1, when t1 is different from a reference time $t_{ref}$ within 15%, the processor 120 may determine that the peaks are periodic.

$$0.85 t_{ref} \leq t1 \leq 1.15 t_{ref} \quad \text{[Equation 1]}$$

For example, tref may be set to an average value of the measured RRIs (t1, t2, t3, t4, and t5). As another example, tref may be a value preset by the user.

According to an exemplary embodiment of the present disclosure, when a predetermined number of biological signals are measured, the processor 120 may determine periodicity for each of the predetermined number of measured biological signals. Referring to FIG. 6, when the six peaks are detected, the processor 120 may determine the periodicity of the biological signal through the five RRI values between the six peaks. The processor 120 may determine whether to compress data for each predetermined number, and selectively perform compression. In another embodiment, the processor 120 may continuously determine the periodicity to perform data compression whenever the compression/decompression determination is changed.

In addition to the ECG shown in FIG. 6, a PPG corresponds to a typical periodic biological signal. The PPG is a method of measuring blood flow by irradiating light to a specific body part and measuring a degree of absorption or reflection in or from the tissue. When the light is irradiated, a degree of transmission of light changes due to hemoglobin changes in the blood, and this change may be attributed to blood flow.

For example, the sensor 110 may measure the PPG using a green light of an LED. The sensor 110 may illuminate the LED green light on a user's specific part (e.g., when the electronic device 100 is implemented as a smart watch on a user's wrist) and measure an amount of absorption of the green light through a photodiode.

Alternatively, the sensor 110 may measure the PPG using a red light or an infrared ray. The sensor 110 may illuminate the red light or the infrared ray on the user's specific part and measure an amount of reflection of the red light or the infrared ray through the photodiode.

In addition to the ECG and the PPG, the sensor 110 may measure various types of biological signals. Then, the processor 120 may compress the plurality of measured biological signals together.

According to an exemplary embodiment of the present disclosure, the processor 120 may determine whether to compress biological signal data according to a motion of the user measured by the motion sensor 130, as well as the characteristic of the biological signal itself measured by the sensor 110. For example, when a degree of motion of the user sensed by the motion sensor 130 is less than or equal to a predetermined threshold value, the processor 120 may compress biological signal data measured by the sensor 110.

Due to the characteristic of the biological signal, when the motion of the user is increased, the repeatability of data is degraded. Using this characteristic, the electronic device 100 according to an exemplary embodiment of the present disclosure may measure the motion of the user using the motion sensor 130 such as an acceleration sensor. The processor 120 may determine a motion state of the user using a value measured by the motion sensor 130. Various kinds of algorithms may be used to determine the motion state of the user, and are not limitedly described in the present specification. As long as it is an algorithm capable of distinguishing the motion state of the user using data of the motion sensor 130, the algorithm may be applicable to the electronic device 100 according to an exemplary embodiment of the present disclosure without limitation.

Figure 7:
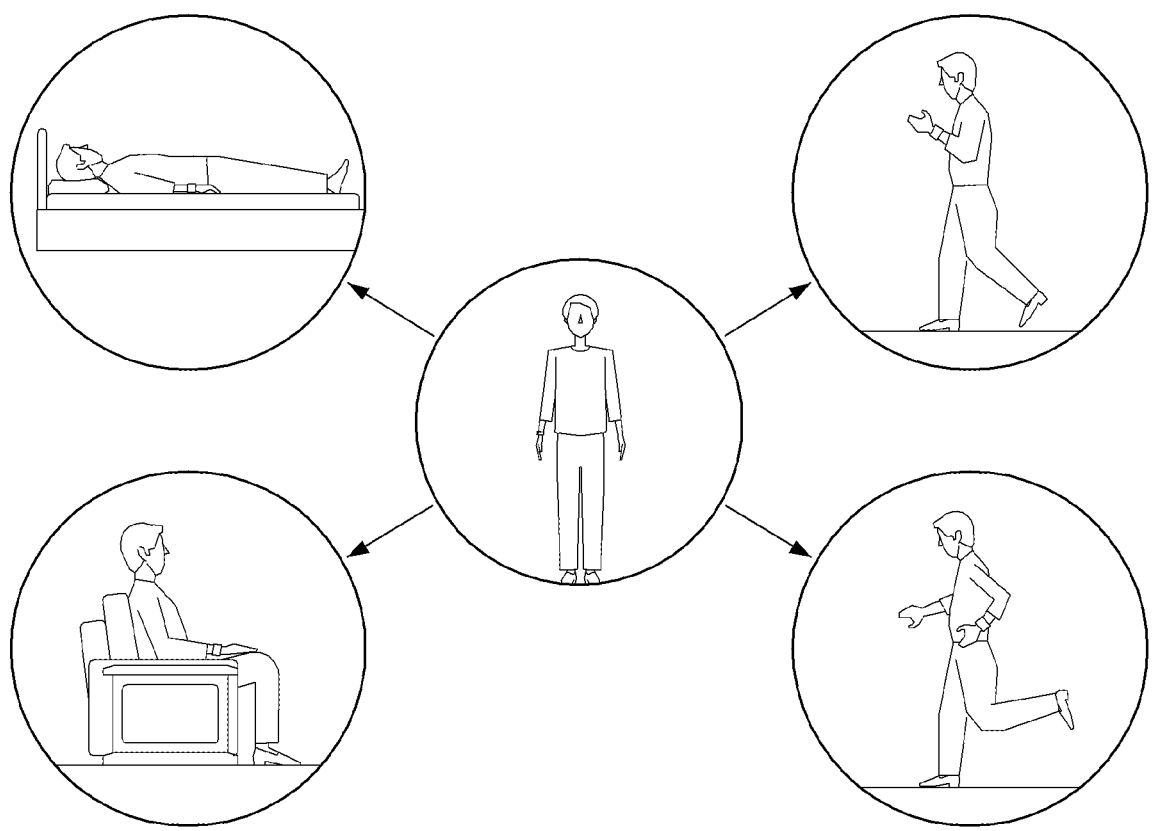
FIG. 7 is a conceptual diagram showing determining a motion of a user that may be determined through a motion sensor.

FIG. 7 is a conceptual diagram showing determining a motion of a user using an acceleration sensor. According to an exemplary embodiment of the present disclosure, the motion sensor 130 may include an acceleration sensor. The processor 120 may determine a state of the user based on a value measured by the acceleration sensor. For example, the processor 120 may determine the state of the user as one of a sleep state, a rest state, a walking state, and a running state.

When the state of the user is determined as the sleep state and the rest state shown in the left side of FIG. 7, the processor 120 may compress a biological signal measured by the sensor 110. When a degree of motion is small, there is a high possibility that the repeatability of the biological signal is maintained. For example, the processor 120 may determine whether to compress the biological signal by comparing a predetermined threshold value with the degree of motion of the user. The processor 120 may compress the biological signal measured by the sensor 110 in the case of the sleep state and the rest state (when the degree of motion of the user is smaller than the predetermined threshold value).

To the contrary, when the state of the user is determined as the walking state and the running state shown in the right side of FIG. 7, the processor 120 may not proceed to compress the biological signal measured by the sensor 110. The processor 120 may store uncompressed data itself in the storage 150 or may control the communicator 140 to transmit the uncompressed data to the external device 200. This is because when the degree of motion is large, the repeatability of the biological signal is generally inferior, and the sensor 110 is likely to measure motion noise together.

The electronic device 100 according to another embodiment of the present disclosure may determine whether to compress the biological signal by determining both the periodicity of the biological signal and the degree of motion of the user.

The processor 120 may determine whether the biological signal measured by the sensor 110 has periodicity. The processor 120 may compare the degree of motion of the user sensed by the motion sensor 130 with a predetermined threshold value.

For example, when the measured biological signal has periodicity and the degree of motion of the user is less than or equal to the predetermined threshold value, the processor 120 may compress the biological signal measured by the sensor 110. In other cases, the processor 120 may not proceed with compression of the measured biological signal.

As described above, the electronic device 100 according to various embodiments of the present disclosure may determine whether to compress the measured biological signal. Hereinafter, an example of a method of compressing data when it is determined that the electronic device 100 compresses the biological signal is described.

Figure 8:
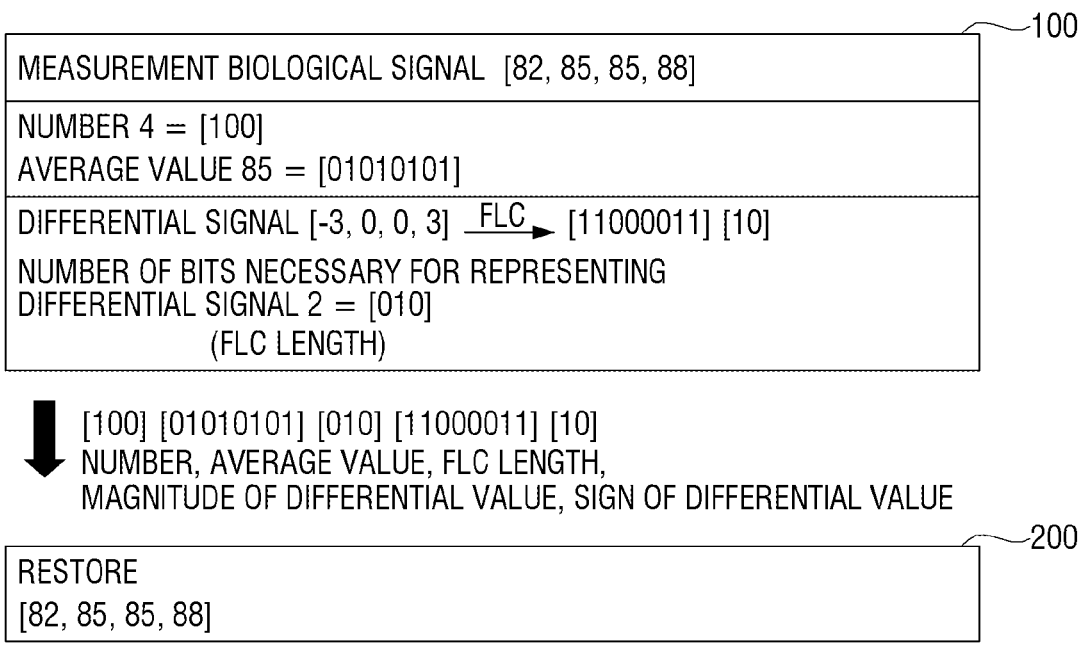
FIG. 8 is a diagram for explaining a data compression method according to an exemplary embodiment of the present disclosure.

FIG. 8 is a diagram for explaining a data compression method of the electronic device 100 according to an exemplary embodiment of the present disclosure. In the embodiment of FIG. 8, the electronic device 100 compresses data and transmits the compressed data to the external device 200, and the external device 200 restores the data. However, an embodiment may be also possible that the electronic device 100 compresses and stores the data therein and restores the stored data again.

Referring to FIG. 8, the processor 120 may control the communicator 140 to calculate the number and an average value of the measured biological signals 82, 85, 85, and 88 and transmit the same to the external device 200. The number of the biological signals is 4 and the average value is 85, and thus the processor 120 may convert the same into binary numbers and transmit [100] [01010101].

The reason why the processor 120 transmits the number of the biological signals is that it is necessary to know what biological signal is reflected to the average value. The reason why the processor 120 transmits the average value is to restore a differential value to be transmitted.

The processor 120 may generate the differential signal using the average value of the measured biological signals. In the example of FIG. 8, the processor 120 may generate the differential signal of [82-85, 85-85, 85-85, 88-85]=[−3, 0, 0, 3].

The processor 120 may calculate the number of bits used to represent the generated differential signal. This is to transmit the differential signal in a FLC (Fixed Length Code) method. As compared with the variable length code (VLC) method, the FLC method has the advantage of knowing the start and end of each data. In the example of FIG. 8, the processor 120 may calculate the number of bits (FLC length) used to represent the differential signal as 2.

The processor 120 may control the communicator 140 to transmit the FLC length, a magnitude of the differential signal, and a sign of the differential signal to the external device 200. In the example of FIG. 8, the FLC length is 2, the magnitude of the differential signal is [3, 0, 0, 3], and the sign of the differential signal is [−, 0, 0, +]. When the differential signal is 0, it is unnecessary to transmit information corresponding to the sign. The processor 120 may convert each into a binary number and transmit [010] [11000011] [10].

The processor 120 may compress and restore biological signal data through the above-described method. However, the biological signal may not limitedly be compressed or restored by the above-described algorithm, and the algorithm shown in FIG. 8 corresponds to only one example applicable to the electronic device 100 according to an exemplary embodiment of the present disclosure. When it is determined that the electronic device 100 according to an exemplary embodiment of the present disclosure performs compression according to the criteria described above, the electronic device 100 may compress the biological signal data using various compression algorithms.

The processor 120 may be implemented as a single element such as one MCU, and an element determining whether to perform compression and an element performing compression may be implemented as separate chips.

Figure 9:
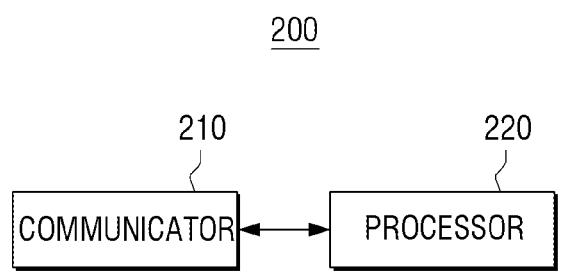
FIG. 9 is a block diagram for explaining a configuration of an analysis device according to an exemplary embodiment of the present disclosure.

FIG. 9 is a block diagram for explaining a configuration of the external device 200 according to an exemplary embodiment of the present disclosure. Referring to FIG. 9, the external device 200 may include a communicator 210 and a processor 220.

The communicator 210 may receive compressed biological signal data or non-compressed biological signal data from the electronic device 100.

The processor 220 may post-process and analyze the biological signal data received through the communicator 210. When the communicator 210 receives the compressed biological signal data, the processor 220 may decompresses the biological signal data to restore biological signal data. Hereinafter, a process, performed by the processor 220, of restoring the biological signal data will be described with reference to FIG. 8.

The processor 220 may restore the biological signal using received [100] [01010101] [010] [11000011] [10]. In FIG. 8, it is described that the number of biological signals, an average value, a FLC length, a magnitude of a differential signal, and a sign of the differential signal are transmitted sequentially, but the present disclosure is not limited to the order.

The processor 220 may restore the number of biological signals as 4 from [100]. Then, the processor 220 may restore the average value of the biological signals as 85 from [01010101].

Also, it may be seen that the processor 220 needs to cut off and interpret the FLC lengths [010] to [11000011] by two. The processor 220 may interpret the magnitude of the differential signal by 2 bits to restore values [3, 0, 0, 3]. The processor 220 may further analyze 1 bit information corresponding to the sign with respect to a value other than 0. Accordingly, the processor 220 may restore the differential signal as [−3, 0, 0, 3]. Finally, the processor 220 may restore the biological signals of [82, 85, 85, 88] using the average value and the differential signal.

Figure 10:
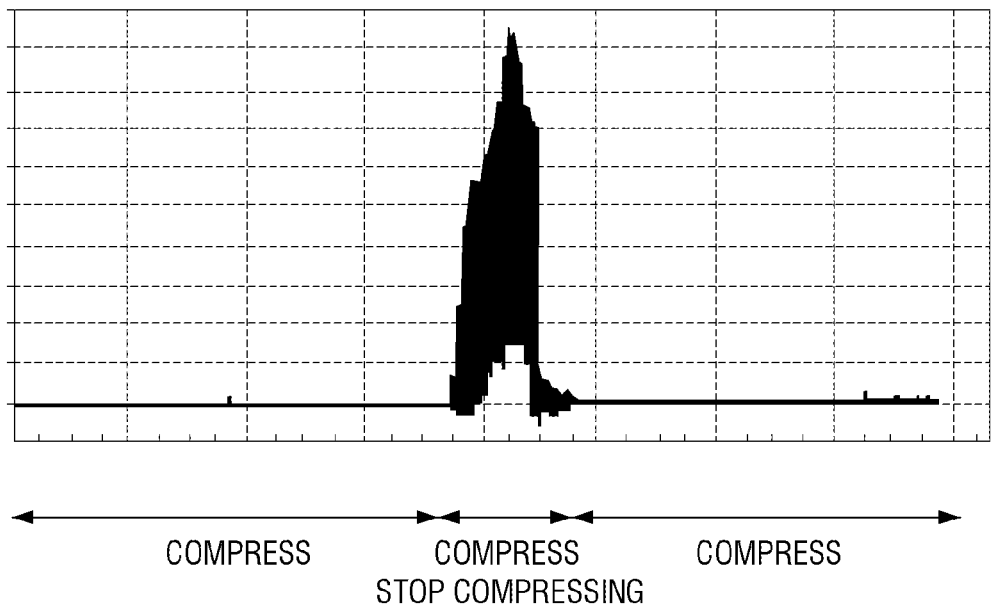
FIG. 10 is a diagram for explaining an electronic device monitoring compressed data according to an exemplary embodiment of the present disclosure.

FIG. 10 is a diagram for explaining the electronic device 100 monitoring compressed data according to an exemplary embodiment of the present disclosure.

The processor 120 may monitor the size of biological signal data in real time. Thus, the processor 120 may monitor the compression efficiency. For example, the processor 120 may control the display 160 to display a GUI provided with the size of the biological signal data, whether to compress of the biological signal data, and the like as shown in FIG. 10.

In an exemplary embodiment, the processor 120 may use the monitored compression efficiency to determine whether to stop compression. The processor 120 may stop the compression of a measured biological signal when the compression efficiency is lower than or equal to a predetermined level.

In another embodiment, the processor 120 may perform feedback on criterion as to whether to compress a biological signal using the monitored compression efficiency. For example, the processor 120 may monitor the compression efficiency and adjust a predetermined range used to determine that intervals between a plurality of peaks are constant.

Through the electronic device 100 according to various embodiments as described above, a section in which data compression of a biological signal is efficiently performed may be determined. Therefore, the data compression efficiency may be increased. As the data compression efficiency increases, an amount of power consumption incurred in data transmission and storage may be reduced, a transmission time may be shortened, and the storage memory capacity may reduced. Also, as the compressed data is stored and transmitted, a security problem with respect to the biological signal data may also be solved.

Figure 11:
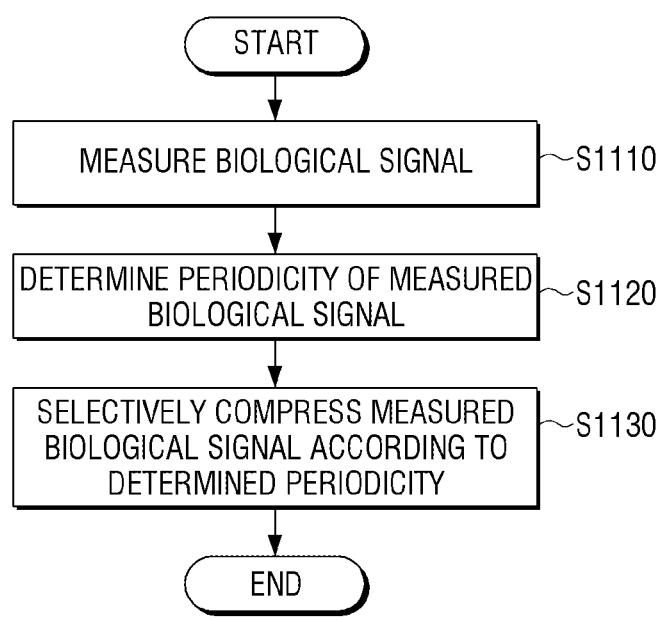
FIGS. 11 to 13 are flowcharts illustrating a signal processing method of an electronic device according to various embodiments of the present disclosure.
Figure 12:
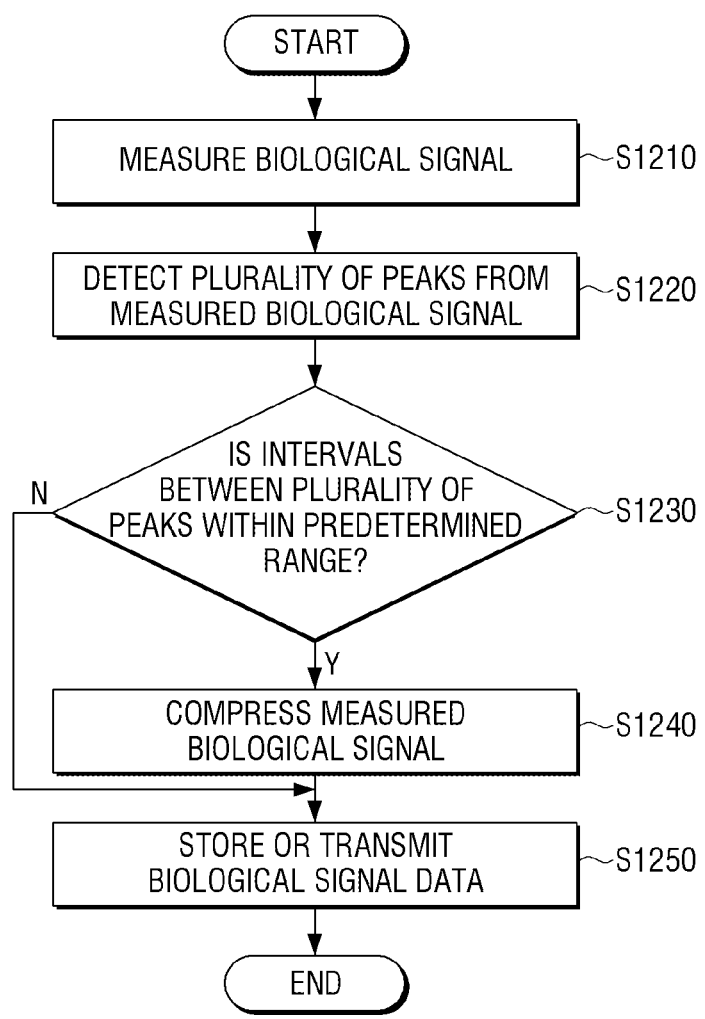
Figure 13:
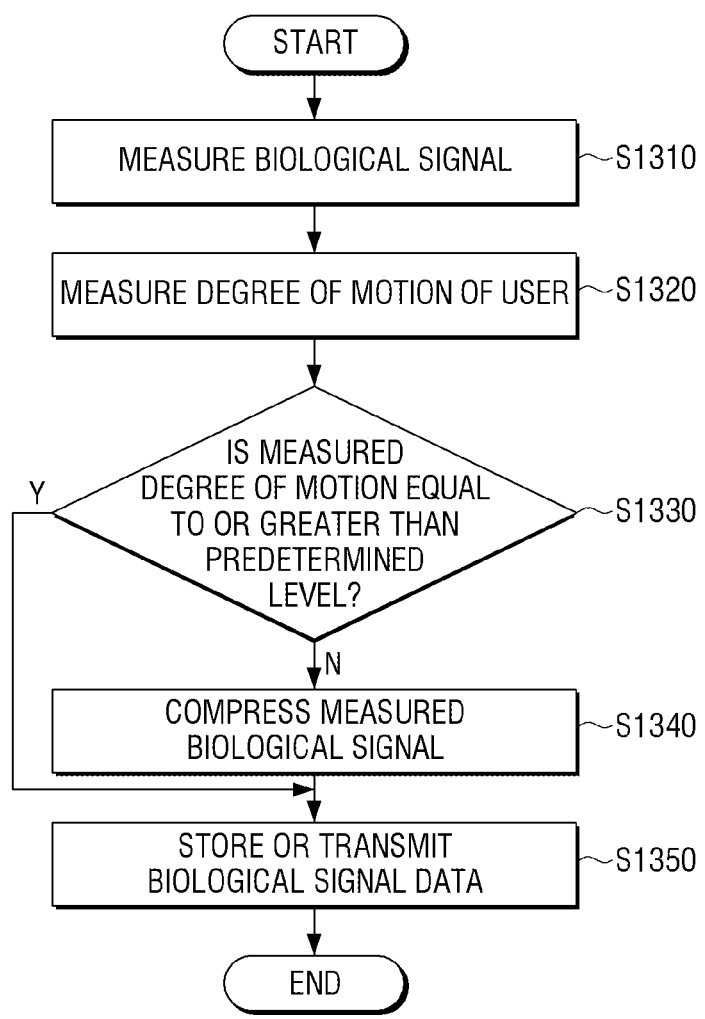

FIGS. 11 to 13 are flowcharts illustrating a signal processing method of the electronic device 100 according to various embodiments of the present disclosure.

Referring to FIG. 11, the electronic device 100 may measure a biological signal of a user (S1110). For example, the electronic device 100 may measure the biological signal of the user using various kinds of analog front ends (AFEs). Examples of measurable biological signals include ECG, EEG, EMG, EOG, and PPG.

Subsequently, the electronic device 100 may determine the periodicity of the measured biological signal (S1120). For example, the electronic device 100 may detect a plurality of peaks from the measured biological signal and determine whether intervals between the detected peaks are constant within a predetermined range. In the case of repetitive data, since the compression efficiency is high, the electronic device 100 may determine the periodicity of the measured biological signal to determine whether the measured biological signal corresponds to the repetitive data.

The electronic device 100 may selectively compress the measured biological signal according to the determined periodicity (S1130). When it is determined that the measured biological signal is a periodic signal, the electronic device 100 may perform a compression process on the measured biological signal. To the contrary, when it is determined that the measured biological signal is aperiodic, the electronic device 100 may store the measured biological signal in an uncompressed state, or may transmit the measured biological signal to the external device 200.

FIG. 12 is a flowchart for explaining a signal processing method of the electronic device 100 according to an exemplary embodiment of the present disclosure. The embodiment of FIG. 12 shows a method of determining whether to compress a biological signal by determining the periodicity of a measured biological signal.

Referring to FIG. 12, the electronic device 100 may measure the biological signal of a user (S1210). Then, the electronic device 100 may detect a plurality of peaks from the measured biological signal of the user (S1220). When it is impossible to detect a peak, the electronic device 100 may store the measured biological signal in an uncompressed state or transmit the measured biological signal to the external device 200.

Even when the plurality of peaks are detected, the electronic device 100 may determine the periodicity of the biological signal based on intervals between the detected plurality of peaks. The electronic device 100 may determine whether the intervals between the plurality of peaks are within a predetermined range (S1230). For example, when the intervals between the plurality of peaks differs by 15% or less from a reference interval value, the electronic device 100 may determine that the measured biological signal is periodic. The reference interval value may be an average value of the intervals between the measured peaks or a predetermined value. Then, the electronic device 100 may adjust the predetermined reference value or the predetermined range (for example, 15%) by monitoring the compression efficiency.

When the intervals between the plurality of peaks are within the predetermined range (S1230-Y), the electronic device 100 may compress the measured biological signal (S1240). The electronic device 100 may compress the measured biological signal using various compression algorithms. Also, the electronic device 100 may perform compression and additionally perform an encryption process. Then, the electronic device 100 may store or transmit the compressed biological signal data (S1250).

For example, the electronic device 100 may compress the measured biological signal using the number of measured biological signals, an average value, and a differential signal. The electronic device 100 may generate the differential signal using the average value of the measured biological signals. Then, the electronic device 100 may compress the measured biological signal using the generated differential signal and the number of bits for representing the generated differential signal.

When the intervals between the plurality of peaks exceed the predetermined range (S1230-N), the electronic device 100 may store or transmit the measured biological signal in an uncompressed state (S1250).

FIG. 13 is a flowchart for explaining a signal processing method of the electronic device 100 according to an exemplary embodiment of the present disclosure. The embodiment of FIG. 13 illustrates a method of determining a motion state of a user from a degree of motion of the electronic device 100 and determining whether to compress a biological signal based on the determined motion state.

Referring to FIG. 13, the electronic device 100 may measure the biological signal of the user (S1310). Then, the electronic device 100 may further measure the degree of motion of the user (S1320). For example, the electronic device 100 may measure the degree of motion of the user of the electronic device 100 by measuring the degree of motion of the electronic device 100 using an acceleration sensor.

The electronic device 100 may determine the motion state of the user using various algorithms. The electronic device 100 may determine the state of the user as one of a sleep state, a rest state, a walking state, and a running state based on a value measured by the acceleration sensor. In addition to the acceleration sensor, the electronic device 100 may also determine the state of the user by combining measured biological signals. For example, the electronic device 100 may determine that the user is in the sleep state by combining the value measured by the acceleration sensor with a measurement value of an EEG.

In the embodiment of FIG. 13, the electronic device 100 may determine whether to compress the biological signal according to the measured degree of motion (S1330). When the measured degree of motion is equal to or greater than a predetermined level (S1330-Y), the electronic device 100 may store or transmit the measured biological signal in a non-compression state (S1350). In general, when the degree of motion is large, the biological signal has no repetitive data form. When the data is not repetitive, the compression efficiency is extremely low even if compression is performed, and in some cases, the data size rather increases.

When the measured degree of motion is less than or equal to the predetermined level (S1330-N), the electronic device 100 may compress the measured biological signal (S1340). For example, the electronic device 100 may calculate the number and an average value of the measured biological signals. Then, the electronic device 100 may generate a differential signal from the measured biological signal using the average value. The electronic device 100 may calculate the number of bits for representing the differential signal, magnitude of the differential signal, and a sign of the differential signal. The electronic device 100 may compress biological signal data by storing or transmitting the number of the biological signals, the average value, the number of bits for representing the differential signal, the magnitude of the differential signal, and the sign of the differential signal.

Finally, the electronic device 100 may store the compressed biological signal data or uncompressed biological signal data or may transmit the compressed biological signal data or the uncompressed biological signal data to the external device 200 (S1350). At this time, the electronic device 100 may additionally perform an encryption process for security.

The electronic device 100 may restore and analyze stored biological information as needed. Alternatively, the electronic device 100 may restore, post-process, and analyze the biological information received from the electronic device 100.

According to the signal processing method of the electronic device 100 according to various embodiments of the present disclosure as described above, the biological signal data may be selectively compressed. Such selective compression results in an increase in the compression efficiency.

The above-described methods may be implemented in the form of program instructions that may be executed through various computer means and recorded in a computer-readable medium. The computer-readable medium may include program instructions, data files, data structures, and the like, alone or in combination. The program instructions recorded on the medium may be those specially designed and constructed for the present disclosure or may be available to those skilled in the art of computer software. Examples of the computer-readable medium include magnetic media such as hard disks, floppy disks, and magnetic tape, optical media such as CD-ROMs and DVDs, magneto-optical media such as floptical disks, and hardware devices specifically configured to store and execute program instructions such as ROM, RAM, flash memory, and the like. Examples of program instructions include machine language code such as those generated by a compiler, as well as high-level language code that may be executed by a computer using an interpreter or the like. The above hardware devices may be configured to operate as one or more software modules to perform the operations of the present disclosure, and vice versa.

Although the present disclosure has been described with reference to certain exemplary embodiments and drawings, it should be understood that the present disclosure is not limited to the above-described embodiments, and that various modifications and changes may be made thereto by those skilled in the art. Therefore, the scope of the present disclosure should not be limited to the embodiments described, but should be determined by equivalents to the appended claims, as well as the appended claims.

The invention claimed is:

1. A biological signal measuring device comprising:
a sensor configured to measure a biological signal of a user, the biological signal comprising at least one of an electrocardiogram, an electroencephalography, an electromyography, an electrooculography, and a photoplethsmography; and
a processor configured to:
  determine a periodicity of the measured biological signal based on whether a fluctuation of intervals between a plurality of peaks in the measured biological signal is within a predetermined range; and
  selectively compress the measured biological signal according to the determined periodicity by compressing the measured biological signal if the measured biological signal is a periodic signal and not compressing the measured biological signal if the measured biological signal is an aperiodic signal, wherein the processor is further configured to adjust the predetermined range by monitoring a compression efficiency corresponding to the compressed biological signal, and wherein the processor is further configured to generate a differential signal by using an average value of the measured biological signal and compress the measured biological signal by using the generated differential signal and a number of bits for representing the generated differential signal.

2. The biological signal measuring device as claimed in claim 1, further comprising a motion sensor comprising at least one of an acceleration sensor, an angular velocity sensor, or a geomagnetic sensor, the motion sensor being configured to sense a degree of motion of the user, wherein the processor is further configured to, based on the sensed degree of motion being less than or equal to a predetermined threshold value and the measured biological signal being the periodic signal, compress the measured biological signal.

3. The biological signal measuring device as claimed in claim 1, wherein the processor is further configured to detect the plurality of peaks from the measured biological signal and determine the periodicity of the biological signal based on the intervals between the detected plurality of peaks.

4. The biological signal measuring device as claimed in claim 1, wherein based on a predetermined number of biological signals are measured, the processor is further configured to determine a periodicity of the measured predetermined number of biological signals.

5. The biological signal measuring device as claimed in claim 1, wherein the processor is further configured to stop compressing the measured biological signal when the compression efficiency is less than or equal to a predetermined level.

6. The biological signal measuring device as claimed in claim 1, further comprising a communicator configured to communicate with an external device, wherein the processor is further configured to control the communicator to transmit the compressed biological signal.

7. The biological signal measuring device as claimed in claim 1, further comprising a storage configured to store the compressed biological signal.

8. The biological signal measuring device as claimed in claim 1, wherein the sensor is configured to measure a plurality of kinds of biological signals of the user, and wherein the processor is further configured to compress the measured plurality of kinds of biological signals together.

9. A biological signal measuring device comprising:

a sensor configured to measure a biological signal of a user, the biological signal comprising at least one of an electrocardiogram, an electroencephalography, an electromyography, an electrooculography, and a photoplethsmography;

a motion sensor configured to sense a degree of motion of the user; and a processor configured to:

determine whether the measured biological signal is a periodic signal based on whether a fluctuation of intervals between a plurality of peaks in the measured biological signal is within a predetermined range;

based on the sensed degree of motion being less than or equal to a predetermined threshold value and the measured biological signal being the periodic signal, compress the measured biological signal; and adjust the predetermined range by monitoring a compression efficiency corresponding to the compressed biological signal, wherein the processor is further configured to generate a differential signal by using an average value of the measured biological signal and compress the measured biological signal by using the generated differential signal and a number of bits for representing the generated differential signal, and wherein the motion sensor comprises an acceleration sensor and is further configured to determine a state of the user as one of a sleep state, a rest state, a walking state, and a running state based on a value measured by the acceleration sensor.

10. A signal processing method of a biological signal measuring device, comprising:

measuring a biological signal of a user;

determining a periodicity of the measured biological signal based on whether a fluctuation of intervals between a plurality of peaks in the measured biological signal is within a predetermined range;

selectively compressing the measured biological signal according to the determined periodicity by compressing the measured biological signal if the measured biological signal is a periodic signal and not compressing the measured biological signal if the measured biological signal is an aperiodic signal; and adjusting the predetermined range by monitoring a compression efficiency corresponding to the compressed biological signal, wherein the biological signal is at least one of an electrocardiogram, an electroencephalography, an electromyography, an electrooculography, and a photoplethsmography, wherein the compressing the measured biological signal comprises generating a differential signal by using an average value of the measured biological signal and compressing the measured biological signal by using the generated differential signal and a number of bits for representing the generated differential signal.

11. The signal processing method as claimed in claim 10, further comprising: sensing a degree of motion of the user, wherein the compressing further comprises, based on the sensed degree of motion being less than or equal to a predetermined threshold value and the measured biological signal being the periodic signal, compressing the measured biological signal.

12. The signal processing method as claimed in claim 10, wherein the determining of the periodicity comprises:

detecting the plurality of peaks from the measured biological signal; and determining the periodicity of the biological signal based on the intervals between the detected plurality of peaks.

* * * * *